(12) United States Patent
Hansen et al.

(10) Patent No.: US 11,678,793 B2
(45) Date of Patent: Jun. 20, 2023

(54) ENDOSCOPE

(71) Applicant: AMBU A/S, Ballerup (DK)

(72) Inventors: Frederik Clausager Vemb Hansen, Ballerup (DK); Ken Henrik Buch, Ballerup (DK)

(73) Assignee: AMBU A/S, Ballerup (DK)

( * ) Notice: Subject to any disclaimer, the term of this patent is extended or adjusted under 35 U.S.C. 154(b) by 85 days.

(21) Appl. No.: 17/504,008

(22) Filed: Oct. 18, 2021

(65) Prior Publication Data

US 2022/0117462 A1    Apr. 21, 2022

(30) Foreign Application Priority Data

Oct. 20, 2020   (EP) .................................... 20202776

(51) Int. Cl.
  *A61B 1/00*   (2006.01)
  *A61B 1/008*  (2006.01)
  *A61B 1/005*  (2006.01)

(52) U.S. Cl.
  CPC ............ *A61B 1/008* (2013.01); *A61B 1/0011* (2013.01); *A61B 1/00045* (2013.01); *A61B 1/0057* (2013.01)

(58) Field of Classification Search
  CPC ... A61B 1/008; A61B 1/00045; A61B 1/0011; A61B 1/0057; A61B 1/00; A61B 1/0055; A61B 1/0125; A61B 1/00073
  USPC ........................................................ 600/141
  See application file for complete search history.

(56) References Cited

U.S. PATENT DOCUMENTS

| | | | |
|---|---|---|---|
| 3,060,972 A | 10/1962 | Sheldon | |
| 4,580,551 A | 4/1986 | Siegmund et al. | |
| 4,651,718 A | 3/1987 | Collins | |
| 4,911,148 A | 3/1990 | Sosnowski et al. | |
| 4,998,916 A | 3/1991 | Hammerslag et al. | |
| 5,089,895 A | 2/1992 | Fraker et al. | |
| 5,176,126 A | 1/1993 | Chikama | |
| 5,178,129 A | 1/1993 | Chikama et al. | |
| 5,376,960 A | 12/1994 | Wurster | |

(Continued)

FOREIGN PATENT DOCUMENTS

| | | |
|---|---|---|
| CN | 109497914 A | 3/2019 |
| EP | 0439931 A1 | 7/1991 |

(Continued)

OTHER PUBLICATIONS

European Extended Search Report in related EP Application No. 20202776.9, dated Apr. 21, 2021.

*Primary Examiner* — Timothy J Neal
*Assistant Examiner* — James Edward Boice
(74) *Attorney, Agent, or Firm* — Faegre Drinker Biddle & Reath LLP

(57) ABSTRACT

An endoscope including a handle and an insertion tube connected to the handle and having a bending section with a first elongate bending section part and a second elongate bending section part. The first elongate bending section part includes first annular members arranged in a row and interconnected by first bridges so as to form a first comb-like structure. The second elongate bending section part includes second annular members arranged in a row and interconnected by second bridges so as to form a second comb-like structure. An outer circumferential surface includes a groove adapted to receive a first bridge and a groove adapted to receive a second bridge of the first bending section part.

19 Claims, 5 Drawing Sheets

(56) References Cited

U.S. PATENT DOCUMENTS

| | | |
|---|---|---|
| 5,379,756 A | 1/1995 | Pileski et al. |
| 5,418,566 A | 5/1995 | Kameishi |
| 5,438,975 A | 8/1995 | Miyagi et al. |
| 5,547,457 A | 8/1996 | Tsuyuki et al. |
| 5,830,401 A | 11/1998 | Prichard et al. |
| 5,966,168 A | 10/1999 | Miyazaki |
| 6,004,263 A | 12/1999 | Nakaichi |
| 6,110,104 A | 8/2000 | Suzuki et al. |
| 6,302,616 B1 | 10/2001 | Takahashi |
| 6,456,863 B1 | 9/2002 | Levin et al. |
| 7,455,806 B2 | 11/2008 | Junger et al. |
| 7,758,495 B2 | 7/2010 | Pease et al. |
| 8,182,422 B2 | 5/2012 | Bayer et al. |
| 8,547,424 B2 | 10/2013 | Ishii et al. |
| 10,321,804 B2 | 6/2019 | Jacobsen et al. |
| 2002/0193663 A1 | 12/2002 | Matsuura |
| 2003/0056540 A1 | 3/2003 | Mukasa et al. |
| 2004/0199052 A1 | 10/2004 | Banik et al. |
| 2004/0242963 A1 | 12/2004 | Matsumoto |
| 2005/0070759 A1 | 3/2005 | Armstrong |
| 2005/0075538 A1 | 4/2005 | Banik et al. |
| 2005/0131279 A1 | 6/2005 | Boulais |
| 2005/0140068 A1 | 6/2005 | Junger et al. |
| 2005/0154262 A1 | 7/2005 | Banik et al. |
| 2005/0119527 A1 | 9/2005 | Ellis et al. |
| 2005/0203341 A1 | 9/2005 | Welker et al. |
| 2005/0234499 A1 | 10/2005 | Olson et al. |
| 2006/0178556 A1 | 8/2006 | Hasser et al. |
| 2007/0049800 A1 | 3/2007 | Boulais |
| 2007/0129466 A1 | 6/2007 | Kagawa et al. |
| 2007/0249896 A1 | 10/2007 | Goldfarb et al. |
| 2007/0249907 A1 | 10/2007 | Boulais |
| 2008/0194911 A1 | 8/2008 | Lee |
| 2008/0221393 A1 | 9/2008 | Padget |
| 2008/0242935 A1 | 10/2008 | Inoue |
| 2008/0249483 A1 | 10/2008 | Slenker |
| 2008/0266441 A1 | 10/2008 | Ichimura |
| 2008/0268559 A1 | 10/2008 | Jung |
| 2008/0287741 A1 | 11/2008 | Ostrovsky |
| 2009/0054728 A1 | 2/2009 | Trusty |
| 2009/0105542 A1 | 4/2009 | Kitagawa et al. |
| 2009/0177040 A1 | 7/2009 | Lyons |
| 2009/0209819 A1 | 8/2009 | Kitagawa et al. |
| 2010/0210905 A1 | 8/2010 | Takeuchi et al. |
| 2010/0217082 A1 | 8/2010 | Ito et al. |
| 2010/0280316 A1 | 11/2010 | Dietz et al. |
| 2010/0324367 A1 | 12/2010 | Matsumoto et al. |
| 2011/0034771 A1 | 2/2011 | Konstorum |
| 2011/0230718 A1 | 9/2011 | Akui |
| 2011/0251519 A1 | 10/2011 | Romoscanu |
| 2012/0002981 A1 | 2/2012 | Frassica et al. |
| 2012/0165608 A1 | 6/2012 | Banik et al. |
| 2013/0041223 A1 | 2/2013 | Kato |
| 2013/0090529 A1 | 4/2013 | Boulais |
| 2014/0114129 A1 | 4/2014 | Peh |
| 2014/0210976 A1 | 7/2014 | Lin |
| 2015/0366436 A1 | 12/2015 | Iuel |
| 2016/0051222 A1 | 2/2016 | Imahashi |
| 2016/0101254 A1 | 4/2016 | Hansen |
| 2018/0325357 A1 | 11/2018 | Boulais |
| 2019/0133705 A1 | 5/2019 | Riojas et al. |
| 2019/0175007 A1 | 6/2019 | Sørensen et al. |
| 2021/0137354 A1 | 5/2021 | Bob et al. |

FOREIGN PATENT DOCUMENTS

| | | |
|---|---|---|
| EP | 0139931 A1 | 8/1991 |
| EP | 1994872 A1 | 11/2008 |
| WO | WO 2014/106511 A1 | 7/2014 |
| WO | WO 2019/211456 A1 | 11/2019 |

ENDOSCOPE

CROSS-REFERENCE TO RELATED APPLICATIONS

This application claims the benefit of and priority from European Patent Application No. 20202776.9, filed on Oct. 20, 2020, which is incorporated herein by reference in its entirety.

TECHNICAL FIELD

The present disclosure relates to endoscopes, in particular to articulated bending sections of insertion endoscopes and the manufacturing thereof.

BACKGROUND

Endoscopes are well known devices for visually inspecting inaccessible places such as human body cavities. Typically, the endoscope comprises an elongated insertion tube with a handle at the proximal end as seen from the operator and visual inspections means, such as a built-in camera, at the distal end of the elongated insertion tube. Electrical wiring for the camera and other electronics such as LED lighting run along the inside of the elongated insertion tube from the handle to the tip at the distal end. Instead of using cameras, endoscopes may also be fibre-optic, in which case the optical fibres run along inside of the elongated insertion tube.

In order to be able to manoeuvre the endoscope inside the body cavity, the distal end of the endoscope may comprise a section with increased flexibility, in the following referred to as a bending section. The bending section comprises a number of hinged segments including a proximal segment, a distal segment and a number of intermediate segments, forming an articulated bending section that may be controlled by an operator. Typically, this is done by tensioning or slacking pull wires also running along the inside of the elongated insertion tube from the articulated bending section part to a control mechanism of the handle. Normally the pull-wires are attached to the most distal segment, and run through suitable passages in the intermediate segments and the proximal segment into the main tube of the insertion tube and via the main tube to the operating mechanism at the handle.

Furthermore, a working channel may run along the inside of the insertion tube from the handle to the tip, e.g. allowing liquid to be removed from the body cavity or allowing the insertion of surgical instruments or the like into the body cavity.

WO2014/106511 show an endoscope with such an articulated bending section, where the articulated bending section is an integrally molded single-piece item, i.e. the segments and the interconnecting hinges are molded as one single injection molded item of a suitable plastic material.

Though this bending section has proved very successful in terms of manufacturing and use, there are some drawbacks that arise from the desire to make the bending section both longer and thinner, i.e. longer length and more segments as well as a smaller outer diameter. More specifically, the passages or apertures for the pull-wires become very narrow, and with the increased length the retractable cores that are used within the mold cavity in the molding process for providing these passages become very long and thin, and thus more prone to failure.

SUMMARY

Based on this it is the object of the present disclosure to provide a novel bending section that overcomes the above drawbacks.

According to a first aspect of the disclosure this object is achieved by an endoscope comprising a handle at the proximal end, an insertion tube connected to the handle, the insertion tube comprising a main tube, a bending section and a tip part at the distal end of the bending section, said endoscope comprising a first control wire and a second control wire for controlling said bending section, said bending section comprising a first elongate bending section part and a second elongate bending section part, said first elongate bending section part comprising a number of first annular members, the first annular members being arranged in a row and interconnected by a number of first bridges so as to form a first comb-like structure, said second elongate bending section part comprising a number of second annular members, the second annular members being arranged in a row and interconnected by a number of second bridges so as to form a second comb-like structure, wherein said first annular members each comprise an outer circumferential surface and an inner circumferential surface and said second annular members each comprise an outer circumferential surface and an inner circumferential surface, and wherein the outer circumferential surface of at least some of said first annular members comprise a groove adapted to receive and accommodate a second bridge of said second bending section part and the outer circumferential surface of at least some of said second annular members comprise a groove adapted to receive and accommodate a first bridge of said first bending section part.

This allows the first and second bending section parts to be formed with only one single lumen each during injection molding. This, in turn, makes it possible to use one large single longitudinal core extending along the length of the bending sector part in the mold. This large single longitudinal core will have much greater mechanical strength and ruggedness, than will the thin cores needed for the control wire passages in the prior art, thus providing for a much more reliable molding process. Another advantage is that the bridges between segments become longer than if they were just attached as hinges to the neighbouring segment as in the prior art, allowing them to bend also where they lie along complementary segments of the other part. Thus, the bending stresses, are to some degree distributed along the entire distance between two segments of the same part, rather than over only the distance between two neighbouring segments in the assembled bending section.

According to a second aspect of the disclosure, the object is solved by a method for providing a bending section of an endoscope, said method comprising: providing a first elongate bending section part comprising a number of first annular members, the first annular members being arranged in a row and interconnected by a number of first bridges so as to form a first comb-like structure, providing a second elongate bending section part comprising a number of second annular members, the second annular members being arranged in a row and interconnected by a number of second bridges so as to form a second comb-like structure, joining the first and second elongate bending section parts by relatively moving them towards each other while keeping the first and second number of bridges in a respective first and second plane, wherein said first and second plane do not coincide.

This sideways joining of the two elongate bending section parts highly facilitates the assembly procedure, in turn allowing for the manufacturing of the two bending sections parts to be simplified.

According to a third aspect of the disclosure the object is solved by a system comprising a display unit and an endoscope according to the first aspect.

According to an embodiment of the first aspect of the disclosure, the outer circumferential surface of at least some of the first annular members comprise an external control wire groove to receive and guide the first control wire, and the outer circumferential surface of at least some of the second annular members comprise an external control wire groove to receive and guide the second control wire. This allows for easy placement of the control wires, as unlike in the prior art they need not be treaded through a long narrow passage, spanning the entire length of the bending section.

According to an embodiment of the first aspect of the disclosure, the inner circumferential surface of at least some of the first annular members comprise an internal control wire groove to receive and guide the second control wire, and the inner circumferential surface of at least some of the second annular members comprise internal control wire groove to receive and guide the first control wire. This allows for easy placement of the control wires, as unlike in the prior art they need not be treaded through a long narrow passage, spanning the entire length of the bending section. Moreover, the interior control wire groove of an annular segment helps keeping the control wire in place in the exterior control wire groove in the neighbouring annular segment.

According to an embodiment of the first aspect of the disclosure, the outer circumferential surface of said first and/or second annular members is essentially cylindrical and wherein the groove comprises a recess part and a lateral chamfer part. This allows the first and second elongated bending section parts to be joined in the sideways direction thereby mutually capturing the control wires that have been inserted in each respective bending section part. This, in turn, facilitates the assembly of the bending section.

According to an embodiment of the first aspect of the disclosure, the interior and/or exterior control wire grooves of the first and/or second annular members comprise two oblique slopes leading to a bottom trough with a circular sector shaped cross-section. This allows the correct capturing and accommodation of the respective control wires in the control wire grooves, when assembling the first and second bending section parts.

According to an embodiment of the first aspect of the disclosure, a tube is inserted through both the first annular members and the second annular members. This tube which may constitute the working channel, will then in addition serve to lock the first and second bending section parts to each other in the assembled state of the bending section. Furthermore, the outer wall of the tube may close the interior control wire grooves.

According to an embodiment of the first aspect of the disclosure, first bending section part and said second bending section part are identical. This is advantageous in that only one tool needs to be provided, and two parts can then be molded in one and the same tool. Identical first and second bending sections may then be joined by mutual sliding them into each other and securing them with the tube.

According to an embodiment of the second aspect of the disclosure, said first and second plane are parallel. This allows for simple assembly as, it facilitates the insertion of the control wires of the endoscope into the bending section.

According to an embodiment of the second aspect of the disclosure, said first number of bridges of said first elongate bending section part engage a second number of recesses of the second elongate bending section part. This allows the two bending section parts to be slid sideways into each other and mutually interlock in a desired position.

This interlocking is further improved if according to an embodiment of the second aspect of the disclosure, said second number of bridges of said second elongate bending section part engage a first number of recesses of the first elongate bending section part.

According to an embodiment of the second aspect of the disclosure, a wire is threaded through at least one of said first and second number of annular members, before the first and second bending section parts are joined. This allows the control wire to be inserted into the relatively large central aperture of the annular members, rather than have to be threaded through an aperture matching closely in size the diameter of the wire.

According to an embodiment of the second aspect of the disclosure, a single wire is threaded through said first and second number of annular members and secured at an end segment so as to provide both a first and a second control wire. This further simplifies the assembly process as a single wire looped through each of the bending section parts is easier to control, tighten and align when joining the two bending section parts sideways.

According to an embodiment of the second aspect of the disclosure, a tube is inserted through said first number of annular members and said second number of annular members after the first and second bending section parts have been joined. This efficiently lock the two bending section parts in permanent engagement against any separation in the lateral direction.

According to an embodiment of the second aspect of the disclosure, said first and/or second elongate bending section parts are provided by injection molding. Injection molding is an efficient way of providing large numbers of identical objects.

According to an embodiment of the second aspect of the disclosure said injection molding comprises injecting liquified material into a mold cavity comprising a number of interconnected sub-cavities corresponding to said number of annular members, wherein only some of said sub-cavities comprise external fluid inlets, and wherein said sub-cavities are separated by an odd number of sub-cavities not comprising external fluid inlets, but being filed via those sub-cavities comprising external fluid inlets. Thereby welding zones are avoided in the bridges forming the hinges.

BRIEF DESCRIPTION OF THE DRAWINGS

The disclosure will now be made in greater detail based on non-limiting exemplary embodiments and with reference to the drawings on which.

DETAILED DESCRIPTION

Figure 1:
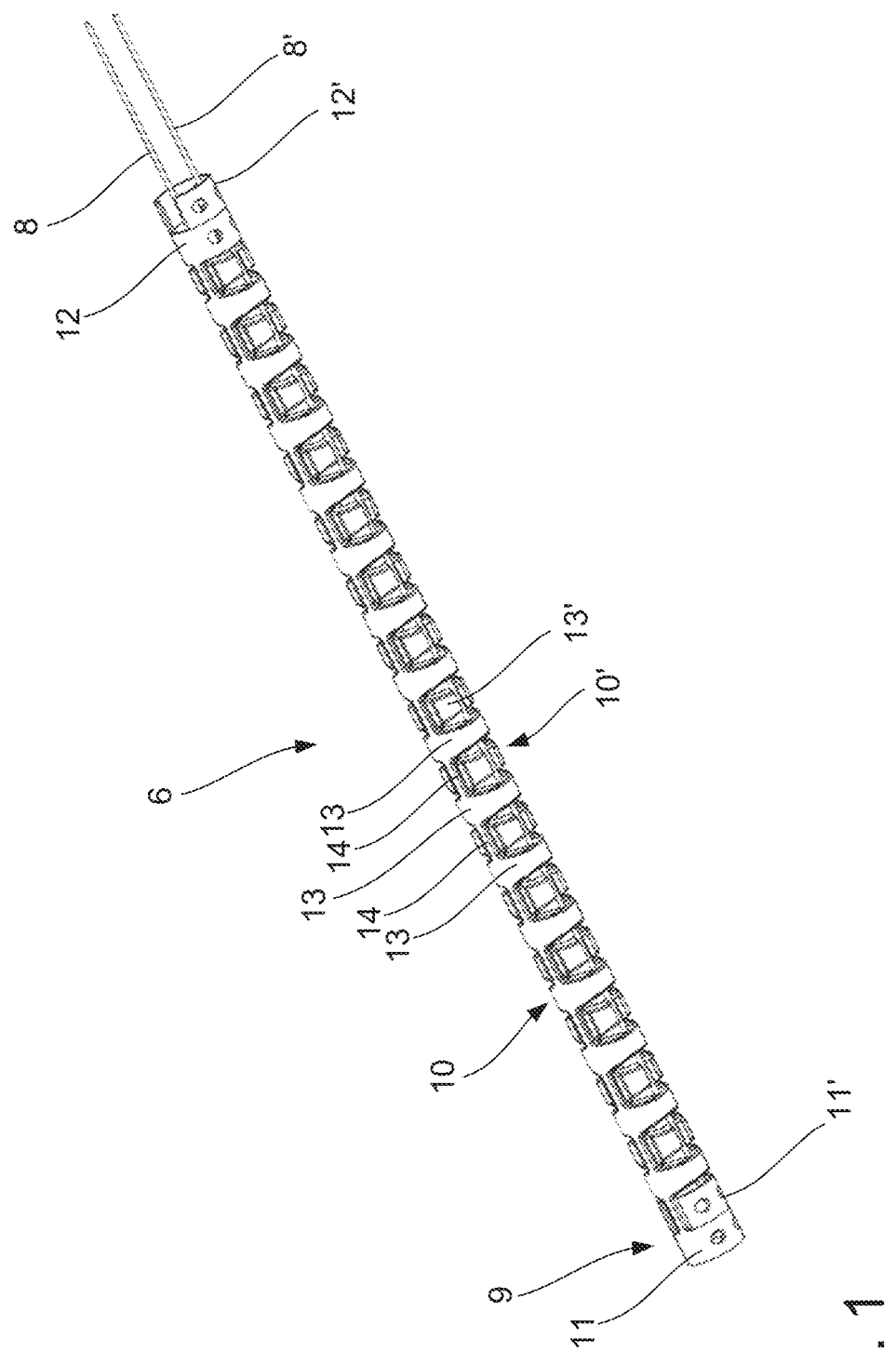
FIG. 1 shows an isometric view from the distal end of a bending section according to the disclosure in the assembled state and including control wires.
Figure 7:
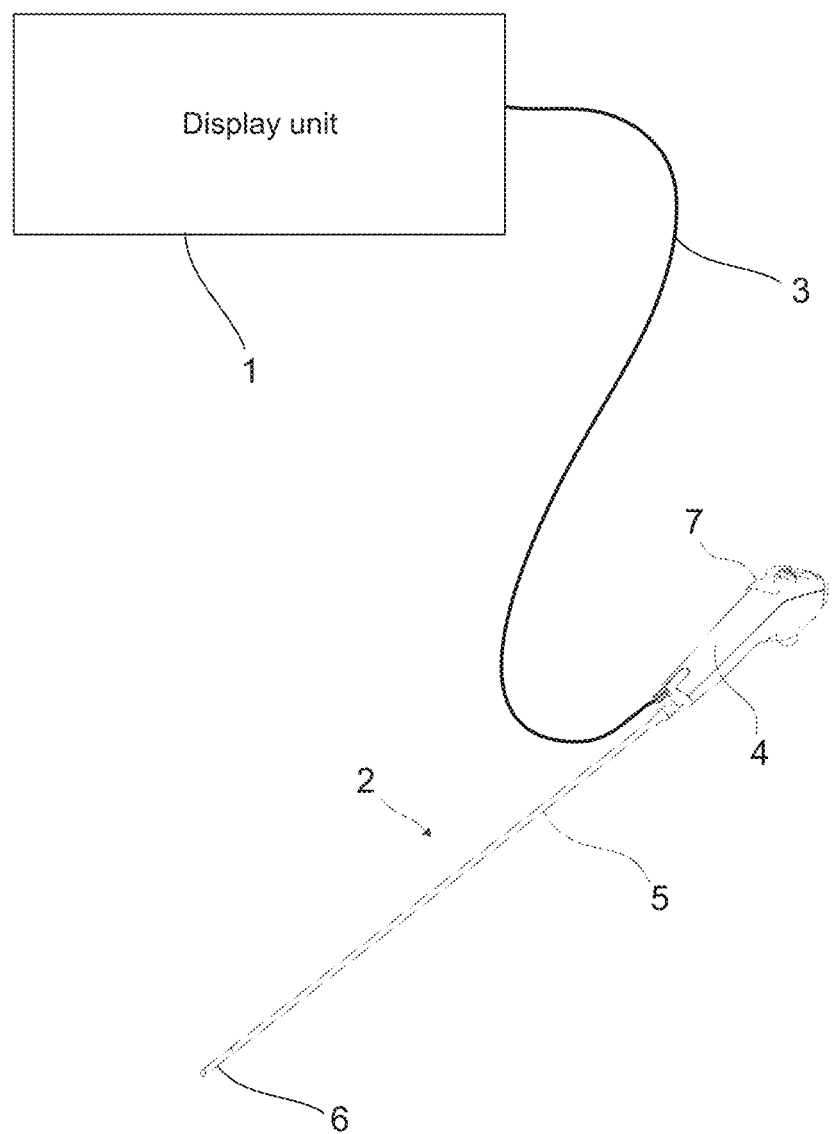
FIG. 7 shows a system comprising a display unit and an endoscope according to the disclosure.

Turning first to FIG. 7 a system comprising a display unit 1, such as a monitor with a screen, and an endoscope 2 connectable thereto via a wireless connection or a cable 3 is shown. The endoscope 2 is preferably a disposable, i.e. single use, endoscope that is to be discarded after use in a patient, rather than cleaned, sterilized and reused. The endoscope 2 comprises a handle 4 at the proximal end adapted to be gripped by the hand of an operator, and a bendable insertion tube 5 extending towards the distal end of the endoscope 2 and adapted to be inserted into a patient. At the distal end of the insertion tube the endoscope comprises a tip part connected to the remainder of the insertion tube, i.e. a main tube part, via an articulated bending section 6. The articulated bending section 6 is highly bendable as compared to the main tube part. The bending motion of the bending section is controlled by the user using an operating member 7 such as knob or a lever via control cables 8, 8' connected to the tip part or the distal end 9 of the bending section 6, as can be seen in FIG. 1. The bending section 6 comprises a thin covering sheath, and the inner details are thus not visible in FIG. 7.

In FIG. 1 the covering sheath and other parts not relevant for the following description has been removed. As can be seen the bending section 6 comprises two mutually engaging bending section parts 10, 10', i.e. a first bending section part 10 and a second bending section part 10'. Both bending section parts 10, 10' are elongated, e.g. with a length of 10 to 20 times, or even longer than 20 times, the largest cross-wise dimension, in the following referred to as diameter.

In the illustrated embodiment the two mutually engaging bending section parts 10 10' are identical, and wherever in the following description there is no need to distinguish the two only the reference numeral without the prime is used, e.g. where a described feature is common to both, and therefore can be described with reference to the same figure, e.g. FIG. 2, 4a or 4b. Of course, one of the two bending section parts can be shorter e.g. have one less segment than the other bending section.

Figure 2:
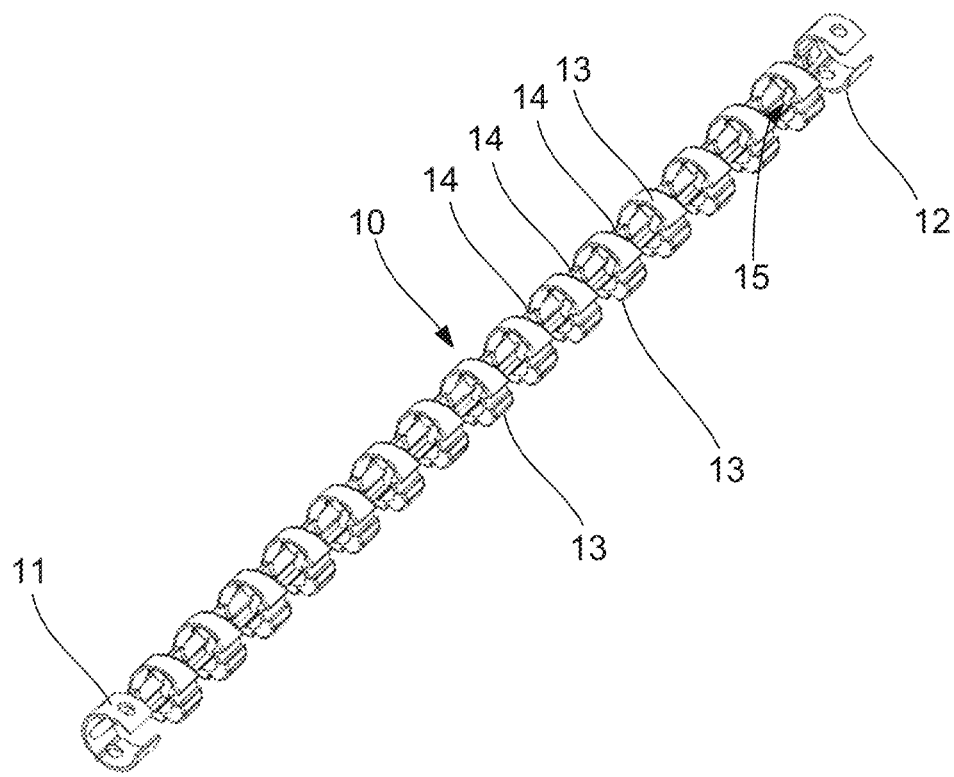
FIG. 2 shows a single bending section part for the use in the bending section of FIG. 1.
Figure 3:
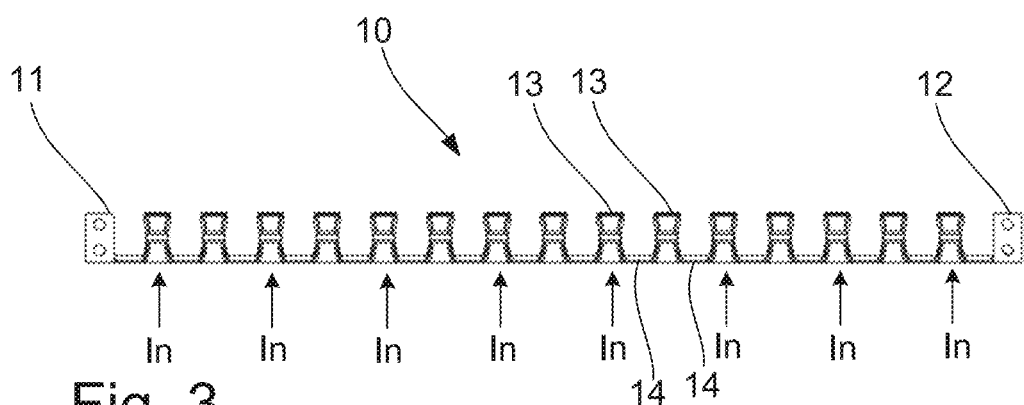
FIG. 3 shows detailed side view of the single bending section part with the comb-like structure clearly visible.

In FIG. 2 one of the bending section parts 10 of FIG. 1 is shown. The bending section part 10 comprises a first end segment 11 and a second end segment 12, which in the illustrated embodiment are identical. Between the first end segment 11 and the second end segment 12 the bending section comprises a number of intermediate segments 13 interconnected and connected in a row with the first end segment 11 and the second end segment 12 by means of a number of bridges 14. The bridges 14 are aligned with each other, e.g. along a line or common axis, when the bending section part is in the, as-made, unbent state, thus giving it the comb-like structure or appearance when seen from the side as shown in FIG. 3. The intermediate segments 13, also referred to as "annular members", are annular and present only one single central aperture 15, that is to say no additional smaller apertures for control wires 8, electrical wiring or the like. The outer circumferential surface is generally cylindrical except for some recesses or grooves to be explained below. Similarly, the inner circumferential surface of the central aperture 15 is largely cylindrical, except for some recesses or grooves to be explained below, and some optional lobes. The first and second end segments 11, 12 are not closed annuli but have through cut-outs. The first and second end segments 11, 12 preferably have the same diameter as the intermediate segments 13. The bending section part 10 thus constitutes what could be termed a comb-like structure, with the bridges 14 forming the back of the comb and the end segments 11, 12 and the intermediate segments 13 forming the teeth of the comb.

Because there is only one relatively larger central aperture 15 it is possible to use a retractable core in the injection molding process that has constant cross-section, rather than as usual a minute taper. Accordingly, all intermediate segments 13 may be made identical. Consequently, the aligned bridges 14 are connected to the identical places along the periphery of the intermediate segments 13. The intermediate segments being identical allows the outer diameter of the bending section part 10, and consequently the entire bending section 6, to be made smaller, than would otherwise be possible in the prior art, because the minimum radial material thickness can be maintained along the entire length and not just be provided at the thicker end of the retractable core, i.e. where the passage formed is wider than the minimum needed at the other end of the bending section.

In the injection molding process it may be advantageous to not have molding inlets at each and every of the segments 13. Rather, by only providing inlets at segments 13 spaced from other segments 13 by an odd number of segments 13 without an inlet it can be avoided that the welding zones where liquified material from two inlets meet and fuse together occur in the bridges 14. Such welding zones may be weaker than the remaining material, and by the use of an odd number spacing these welding zones can be located in the body of a segment 13 rather than in the comparably thinner bridges 14, thus increasing the overall strength of the bending section part 10. In particular the odd number may be one, as indicated by the arrows marking the inlet positions in FIG. 3, so as to keep the flow path from the inlets to the welding zones short. Higher odd numbers such as three, five or more is however not excluded.

In FIG. 3 the bending section part 10 comprises a proximal end segment 12 and a distal end segment 11. Between the proximal end segment 12 and the distal end segment 11 a number of intermediate segments 13 are arranged. In FIG. 2 there are fifteen intermediate segments, so that the entire row of segments totals seventeen but the number of intermediate segments 13 could both be higher or lower depending on the actual design and purpose of the medical device. Between the segments a number of integrally molded bridges 14 that provide the hinge members extends. As mentioned every second segment 13 may have been filled directly from an external fluid inlet of the injection mold in which the bending section part 10 has been molded. Material corresponding to that of the external fluid inlets as such has been broken away after manufacture. The mold comprises a number of sub-cavities, each corresponding to a segment of the resulting bending section part 10, each sub-cavity being separated from its neighbor except for the passages adapted for forming the bridges 14, which thus serve as internal fluid inlets for those sub-cavites. Apart from that the mold comprises at least one retractable and/or collapsible core for forming the single central aperture 15 (not visible in FIG. 3).

As will be understood every second of the sub-cavities does not comprise an external fluid inlet. During injection of the liquified molding material into the mold these sub-cavities will only be indirectly filled with molding material, i.e. via the sub-cavities with the external fluid inlets and through the passages adapted to form the bridges 14. With identical or largely identical sub-cavities and due consideration of the deviations of the sub-cavities for the proximal end segment 12 and the distal end segment 11 an odd number of cavities, in casu one, between each sub-cavity with an external fluid inlet the flows of liquified molding material from two sub-cavities with an external fluid inlet can be made to meet and fuse together in the middle of the intermediate sub-cavities without an external fluid inlet. The welding zone thus occurs in the bulk of the material of the intermediate segment 13 as far away from the more critical bridges 14 as possible.

Figure 4A:
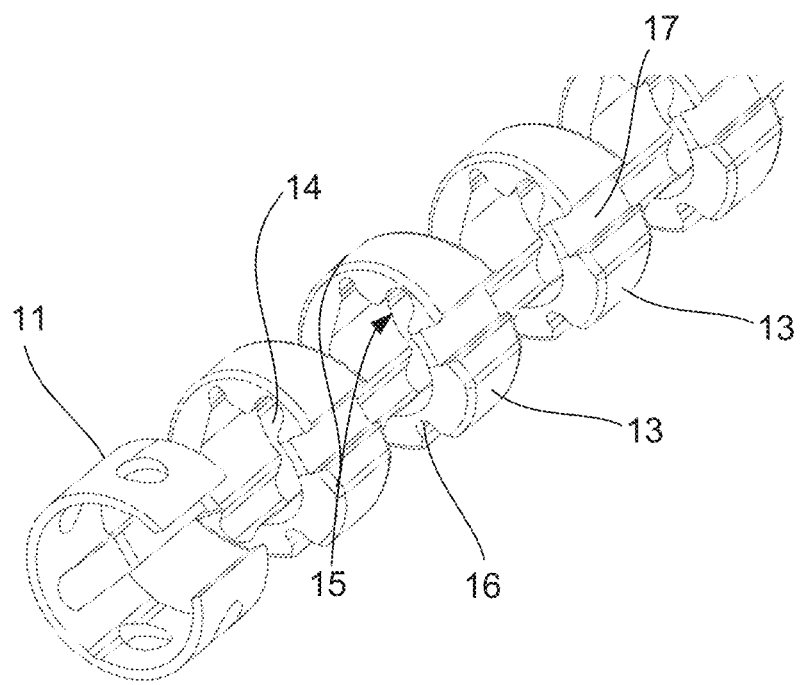
FIG. 4a shows a first detailed view of the single bending section part at an angle.
Figure 4B:
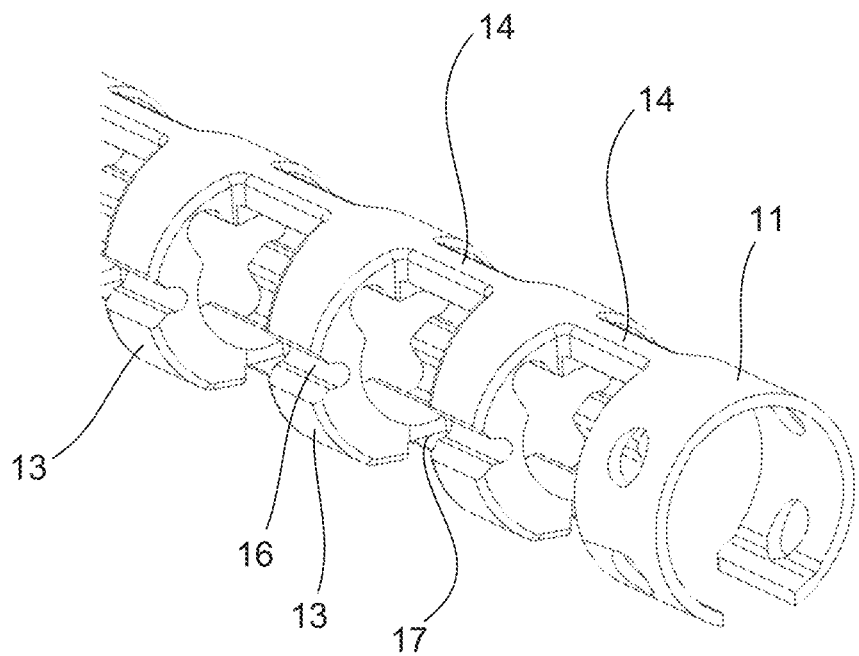
FIG. 4b shows a second detailed view of the single bending section part from another angle.

In FIGS. 4*a* and 4*b* it can better be seen how the outer, generally cylindrical, circumferential surface of the intermediate segments 13 comprise a first groove 16, adapted to serve as a control wire groove adapted for accommodating and guiding a control wire 8 and a second groove 17 adapted to receive a bridge 14' of the complementary bending section part 10', so as to position the first and second bending parts 10, 10' with respect to each other.

Figure 5:
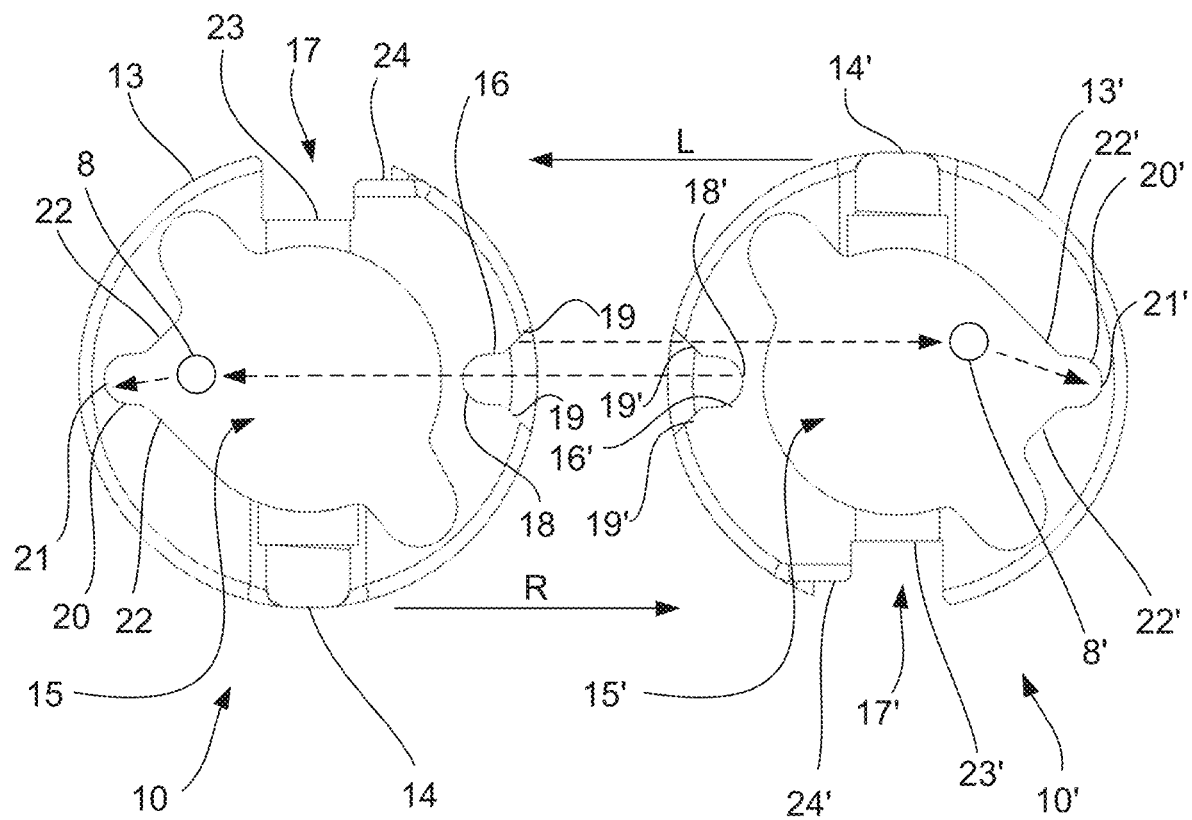
FIG. 5 illustrates the assembly process of two bending section parts to form the bending section of FIG. 1.

As can best be seen in FIG. 5 the first groove 16 comprises a generally U-shaped bottom part 18, with a semi-circular cross-section, and two oblique sides 19 each forming a slope towards to the U-shaped bottom part 18. The diameter of the semi-circular cross-section is preferably only slightly larger than the diameter of the control wire 8', allowing it to accommodate and guide the control wire 8' in a well-defined manner. A third groove 20 adapted to receive and accommodate the second control wire 8 is provided in the surface of the inner circumferential wall of the central aperture 15. The third groove 20 has large similarities with the first groove 16. It thus also presents a bottom 21 which is generally U-shaped, having a semi-circular cross-section with a diameter preferably only slightly larger than the control wire 8, thereby allowing it to accommodate and guide the control wire 8 in a well-defined manner. Like the first groove 16 it also comprises two oblique sides 22 each forming a slope towards to the U-shaped bottom part 21.

Figure 6:
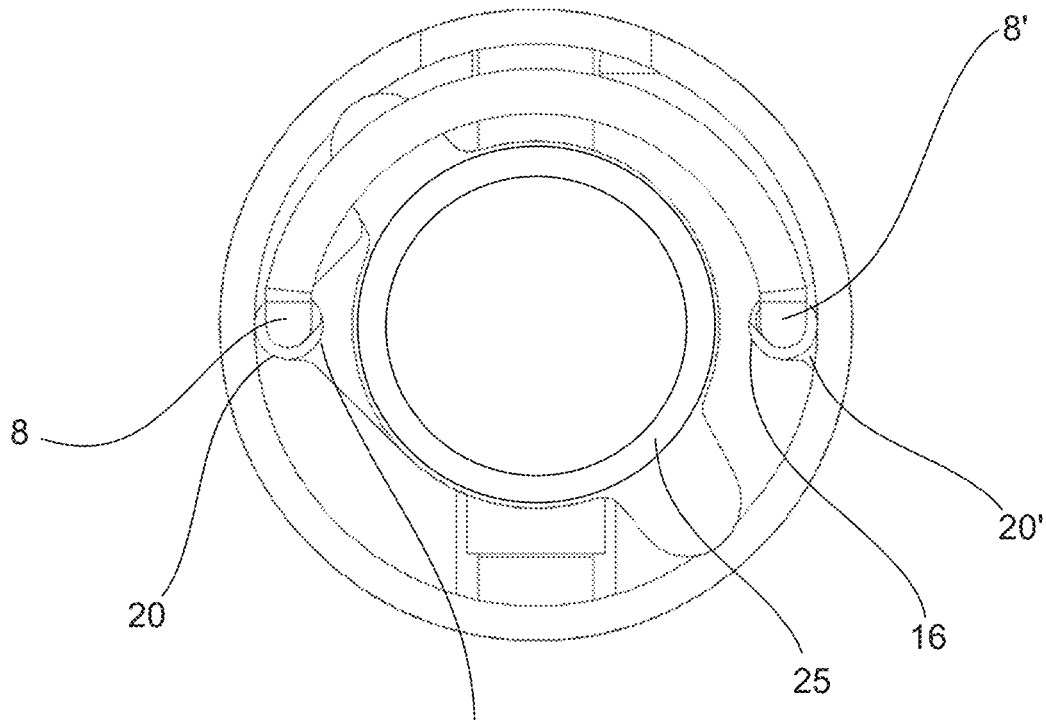
FIG. 6 shows and end view of the distal end of the bending section of FIG. 1.

As can better be seen in FIG. 5 the first bending section part 10 and the second bending section part 10' are joined sideways, that is to say not in the direction of the opposing teeth of the comb-like structure but sideways, i.e. by moving the backs of the two comb-like structure with the bridges 14, 14', respectively, in two parallel planes, i.e. horizontally in FIG. 5 until they lie opposite each other in a common plane perpendicular to the two parallel planes, i.e. what would be vertically above each other in FIG. 5. However, before doing so the control wires 8, 8' are threaded through the central apertures 15, 15' of the intermediate segments along the length of the respective bending section part 10, 10'. In practice, as can be seen in FIG. 6, showing the assembled bending section, the two control wires 8, 8' can advantageously be provided as one single wire, e.g. the two control wires are sections of the single wire. This single wire is then threaded through the first intermediate segment of a first bending section part 10 in one direction towards the distal end and back through the second intermediate segments of a second bending section part 10' in the opposite direction, i.e. in a loop. When the single wire is later secured at the distal end of the assembled bending section 6, the single wire cannot from a pulling perspective be distinguished from two individually secured control wires 8, 8'. The single wire may be secured in any suitable manner known to the skilled person, but gluing is currently preferred.

With the pull-wires 8, 8' treaded through the respective bending section parts 10, 10', the two bending section parts 10, 10' may now be pushed sideways together as explained above and indicated with the left and right arrows L, R in FIG. 5. If a control wire 8 are not perfectly aligned with the U-shaped bottom 21 of one intermediate segment 13 the oblique slopes 22 in conjunction with the oblique slopes 19' of the neighbouring intermediate segments 13' will aid in pushing the control wire into position in the U-shaped bottoms 21, 18' of the first and third grooves of the respective first and second bending section parts 10, 10'.

Accordingly, when the two bending section parts 10, 10' have been pushed together to the resulting configuration shown in FIG. 6, a first control wire 8 will be accommodated in alternating grooves 20, 16' and the second control wire 8' be accommodated between alternating grooves 16, 20'.

To secure this position the bridges 14 of the first bending segment part 10, latch into the second grooves 17' of the second bending segment part 10' and vice versa. To allow for the sideways joining of the first and second bending section parts 10, 10' the second grooves 17, 17' are asymmetrical in cross-section. That is to say, the second groove 17 in the outer circumferential surface of the annular intermediate segments 13, 13' comprises a recess part 23 and a lateral chamfer part 24. Thus when sliding the first and second bending section parts 10, 10' together as illustrated, the bending section parts 10, 10' will deform slightly allowing the first bridges 14 of the first bending section part 10 to slide along part of the outer generally circular circumferential surface of one of the second intermediate segments 13' of the second bending section part 10', along the chamfered surface 24', and latch into the recess 23' in an undeformed relaxed state. The same will happen simultaneously in the opposite direction where allowing the second bridges 14' of the second bending section part 10' slide along a part of the outer generally circular circumferential surface of one of the first intermediate segments 13 of the first bending section part 10, along the chamfered surface 24, and latch into the recess 23 in an undeformed relaxed state. This secures the mutual position of the first and second bending section parts 10, 10' with respect to each other.

To permanently secure the first and second bending section parts in this mutually interlocked position, a tube 25 adapted to serve as a working channel of the endoscope is inserted along the length of the bending section 6 through the central apertures 15, 15' of the intermediate segments 13, 13' of both the first bending section part 10 and the second bending section part 10', The central apertures 15, 15' are largely circular in cross-section, except for inter alia the third grooves 20, 20' described above and optional lobes for other purposes. The outer diameter of the tube 25 is preferably adapted to match the diameter of the largely circular cross-section of the central apertures 15, 15' so that the inserted tube 25 prevents any lateral displacement of the first and second bending section parts 10, 10' an in any lateral direction.

The bending section 6 thus assembled may then be joined to the main tube at the proximal end thereof and to a tip part at the distal end thereof.

The tip part, however, could also form part of one of the first or second bending section parts 10, 10'. It is not necessary for the working of the present disclosure that the first and second bending parts 10, 10' are identical. Thus, the first bending section part 10, could include the tip part as an integral part, e.g. forming the distal end segment 11 accommodating camera, electronics, illumination etc. of the endoscope 2. Similarly, the second bending section 10' could include a proximal end segment 12' especially adapted for connection to the main tube of the endoscope 2. Without departing from the teachings of this disclosure, it can also be envisaged that the first bending section part 10 comprises both an integrally formed tip part as mentioned above and a proximal end segment adapted to be joined to the main tube. In that case the second bending section part may have proximal and distal end segments 11', 12' that are identical to the intermediate segments 13'.

The following items are further examples of various embodiments disclosed above:

Item 1. An endoscope comprising a handle at the proximal end, an insertion tube connected to the handle, the insertion tube comprising a main tube, a bending section and a tip part at the distal end of the bending section, said endoscope comprising a first control wire and a second control wire for controlling said bending section, said bending section comprising a first elongate bending section part and a second elongate bending section part, said first elongate bending section part comprising a number of first annular members, the first annular members being arranged in a row and interconnected by a number of first bridges so as to form a first comb-like structure, said second elongate bending section part comprising a number of second annular members, the second annular members being arranged in a row and interconnected by a number of second bridges so as to form a second comb-like structure, wherein said first annular members each comprise an outer circumferential surface and an inner circumferential surface and said second annular members each comprise an outer circumferential surface and an inner circumferential surface, and wherein the outer circumferential surface of at least some of said first annular members comprise a groove adapted to receive and accommodate a second bridge of said second bending section part and the outer circumferential surface of at least some of said second annular members comprise a groove adapted to receive and accommodate a first bridge of said first bending section part.

Item 2. An endoscope according to item 1, wherein the outer circumferential surface of at least some of the first annular members comprise an external control wire groove to receive and guide the first control wire, and the outer circumferential surface of at least some of the second annular members comprise an external control wire groove to receive and guide the second control wire.

Item 3. An endoscope according to any one of the preceding items, wherein the inner circumferential surface of at least some of the first annular members comprise an internal control wire groove to receive and guide the second control wire, and the inner circumferential surface of at least some of the second annular members comprise internal control wire groove to receive and guide the first control wire.

Item 4. An endoscope according to any one of the preceding items, wherein the outer circumferential surface of said first and/or second annular members is essentially cylindrical and wherein the groove comprises a recess part and a lateral chamfer part.

Item 5. An endoscope according to any one of the preceding items wherein the interior and/or exterior control wire grooves of the first and/or second annular members comprise two oblique slopes leading to a bottom trench with a circular sector shaped cross-section.

Item 6. An endoscope according to any one of the preceding items, wherein a tube is inserted through both the first annular members and the second annular members.

Item 7. An endoscope according to any one of the preceding items wherein said first bending section part and said second bending section part are identical.

Item 8. A method for providing a bending section of an endoscope, said method comprising:

providing a first elongate bending section part comprising a number of first annular members, the first annular members being arranged in a row and interconnected by a number of first bridges so as to form a first comb-like structure, providing a second elongate bending section part comprising a number of second annular members, the second annular members being arranged in a row and interconnected by a number of second bridges so as to form a second comb-like structure, joining the first and second elongate bending section parts by relatively moving them towards each other while keeping the first and second number of bridges in a respective first and second plane, wherein said first and second plane do not coincide.

Item 9. A method according to item 8, wherein said first and second plane are parallel.

Item 10. A method according to item 9, wherein said first number of bridges of said first elongate bending section part engage a second number of recesses of the second elongate bending section part.

Item 11. A method according to items 9 or 10, wherein said second number of bridges of said second elongate bending section part engage a first number of recesses of the first elongate bending section part.

Item 12. A method according to any one of items 8 to 11, wherein a wire is threaded through at least one of said first and second number of annular members, before the first and second bending section parts are joined.

Item 13. A method according to item 12 wherein a single wire is threaded through said first and second number of annular members and secured at an end segment so as to provide both a first and a second control wire.

Item 14. A method according to any one of items 8 to 13, wherein a tube is inserted through said first number of annular members and said second number of annular members after the first and second bending section parts have been joined.

Item 15. A method according to any one of items 8 to 14, wherein said first and/or second elongate bending section parts are provided by injection molding.

Item 16. A method according to item 15, wherein said injection molding comprises injecting liquified material into a mold cavity comprising a number of interconnected sub-cavities corresponding to said number of annular members, wherein only some of said sub-cavities comprise external fluid inlets, and wherein said sub-cavities are separated by an odd number of sub-cavities not comprising external fluid inlets, but being filed via those sub-cavities comprising external fluid inlets.

Item 17. A system comprising a display unit and an endoscope according to any one of items 1 to 7.

We claim:

1. An endoscope comprising:
    a handle;
    an insertion tube connected to the handle, the insertion tube comprising a main tube, a bending section and a tip part at the distal end of the bending section;

wherein the bending section has an inner side and an outer side and comprises:
- a first bending section part including first annular members arranged in a row and interconnected by first bridges so as to form a first comb-like structure; and
- a second bending section part including second annular members arranged in a row and interconnected by second bridges so as to form a second comb-like structure;

wherein at least one of the first annular members comprises an outer groove sized and shaped to receive a second bridge of the second bridges; and wherein at least one of the second annular members comprises an outer groove sized and shaped to receive a first bridge of the first bridges.

2. The endoscope of claim 1, wherein the first bending section part and the second bending section part are identical.

3. The endoscope of claim 1, wherein the first bridges lie in a first plane and the second bridges lie in a second plane different than the first plane.

4. The endoscope of claim 1, further comprising a first control wire and a second control wire for controlling the bending section, wherein at least one of the first annular members comprises an outer control wire groove to receive and guide the first control wire, and wherein at least one of the second annular members comprises an outer control wire groove to receive and guide the second control wire.

5. The endoscope of claim 4, wherein the outer grooves of the first annular members and/or the second annular members each comprises a recess part and a lateral chamfer part.

6. The endoscope of claim 4, wherein at least one of the first annular members comprises an inner control wire groove to receive and guide the second control wire, and wherein at least one of the second annular members comprises an inner control wire groove to receive and guide the first control wire.

7. The endoscope of claim 6, wherein the inner control wire grooves and/or the outer control wire grooves of the first annular members and/or the second annular members each comprises two oblique slopes leading to a bottom trench with a circular sector shaped cross-section.

8. The endoscope of claim 4, wherein the bending section comprises a distal end segment, wherein the first control wire and the second control wire are sections of a single wire, and wherein the single wire is secured to the distal end segment.

9. The endoscope of claim 1, further comprising a tube positioned through both the first annular members and the second annular members.

10. A system comprising:
a display unit; and
the endoscope of claim 1.

11. A method of making an endoscope, the method comprising:
providing a handle;
providing a first bending section part comprising first annular members arranged in a row and interconnected by first bridges so as to form a first comb-like structure;
providing a second bending section part comprising second annular members arranged in a row and interconnected by second bridges so as to form a second comb-like structure;
joining the first bending section part and the second bending section part, to form a bending section, by relatively moving them towards each other while keeping the first bridges and the second bridges in, respectively, a first plane and a second plane, the bending section having an inner side and an outer side,
wherein the first plane and the second plane do not coincide,
wherein at least one of the first annular members comprises an outer groove sized and shaped to receive a second bridge of the second bridges, and
wherein at least one of the second annular members comprises an outer groove sized and shaped to receive a first bridge of the first bridges, and
wherein the method further comprises connecting an insertion tube to the handle, the insertion tube comprising a main tube, the bending section and a tip part at the distal end of the bending section.

12. The method of claim 11, wherein the first plane and the second plane are parallel.

13. The method of claim 12, further comprising engaging the first bridge of the first bending section part onto the outer groove of the at least one of the second annular members of the second bending section part.

14. The method of claim 13, further comprising engaging the second bridge of the second bending section part onto the outer groove of the at least one of the first annular members of the first bending section part.

15. The method of claim 13, further comprising, before joining the first bending section part and the second bending section part, threading a wire through at least one of the first annular members or at least one of the second annular members.

16. The method of claim 15, wherein the bending section comprises a distal end segment, the method further comprising:
threading the wire through the first annular members and the second annular members; and
securing the wire at the distal end segment so as to provide both a first control wire and a second control wire, the first control wire and the second control wire being sections of the wire.

17. The method of claim 11, further comprising, after joining the first bending section part and the second bending section part, inserting a tube through the first annular members and the second annular members.

18. The method of claim 11, further comprising, before said providing, molding the first bending section part and the second bending section part.

19. The method of claim 18, wherein said molding comprises injecting liquified material into a mold cavity comprising a number of interconnected sub-cavities corresponding to the first annular members or the second annular members, wherein only some of the sub-cavities comprise external fluid inlets, and wherein the sub-cavities comprising external fluid inlets are separated by an odd number of sub-cavities not comprising external fluid inlets but being filled via the sub-cavities comprising external fluid inlets.

* * * * *